United States Patent [19]

Goldberg et al.

[11] Patent Number: 5,176,898
[45] Date of Patent: Jan. 5, 1993

[54] AEROSOL HAIRSPRAYS CONTAINING LOW VOC CONTENT

[75] Inventors: Marvin E. Goldberg, Marlboro; Malti Bhambhani, Scotch Plains, both of N.J.; Arthur Brandon, Valley Cottage, N.Y.

[73] Assignee: Revlon Consumer Products Corporation, New York, N.Y.

[21] Appl. No.: 838,987

[22] Filed: Feb. 21, 1992

[51] Int. Cl.$^5$ ............................................. A61K 7/11
[52] U.S. Cl. .................................... 424/47; 424/71
[58] Field of Search ................................. 424/47, 71

[56] References Cited

U.S. PATENT DOCUMENTS

| | | |
|---|---|---|
| 2,826,551 | 3/1958 | Geen ........................ 252/174.15 |
| 4,172,887 | 10/1979 | Vanlerberghe ................. 424/70 |
| 4,374,825 | 2/1983 | Bolich ........................... 424/70 |
| 4,387,090 | 6/1983 | Bolich ........................... 424/70 |
| 4,423,032 | 12/1983 | Abe .............................. 424/70 |
| 4,472,375 | 9/1984 | Bolich, Jr. ..................... 424/70 |
| 4,529,586 | 7/1985 | DeManco ....................... 424/70 |
| 4,543,249 | 9/1985 | Nelson .......................... 424/70 |
| 4,764,363 | 8/1988 | Bolich ........................... 424/47 |
| 4,798,722 | 1/1989 | Edman .......................... 424/72 |
| 4,818,523 | 4/1989 | Clarke .......................... 424/70 |
| 4,871,529 | 10/1989 | Sramek ......................... 424/47 |
| 4,902,499 | 2/1990 | Bolich ........................... 424/70 |
| 4,954,336 | 9/1990 | Chuang ......................... 424/71 |
| 4,983,377 | 1/1991 | Murphy et al. .................. 424/70 |
| 4,983,383 | 1/1991 | Maksimoski .................... 424/47 |
| 5,068,099 | 11/1991 | Sramek ......................... 424/47 |

*Primary Examiner*—Thurman K. Page
*Assistant Examiner*—D. Colucci
*Attorney, Agent, or Firm*—Julie Blackburn

[57] ABSTRACT

An aqueous hair spray composition having low VOC content and a method for styling the hair using the composition of the invention.

16 Claims, No Drawings

5,176,898

AEROSOL HAIRSPRAYS CONTAINING LOW VOC CONTENT

TECHNICAL FIELD

The invention is in the field of aerosol hair spray compositions.

BACKGROUND OF THE INVENTION

VOC's (volatile organic compounds) are widely used as propellants in aerosol spray products such as hair sprays, deodorants, and the like. Some environmentalists believe that VOC's have an adverse effect on the ozone layer of the earth's atmosphere. Thus, environmental lobbies in various states are working toward enacting legislation which reduces or eliminates the use of VOC's in personal care products marketed in the aerosol spray form. Legislation has been enacted in certain states which limits the amount of VOC's in an aerosol product to 80%. It is anticipated that by 1996 only 55% VOC's will be permitted in aerosol spray products.

Aerosol hair sprays are ubiquitous in our society, and are usually anhydrous compositions which contain hair fixative resins in conjunction with a volatile propellant or VOC. The propellant enables the resin to be applied to the hair in a fine dispersed spray which exhibits hair holding power.

If VOC's are reduced or removed from hair sprays, other nonvolatile constituents must be substituted in place of the VOC. There are few nonvolatile liquids which would be suitable, and of those, water is preferred for economic and safety reasons.

However, eliminating or reducing VOC's in anhydrous systems, or moving into low VOC content aqueous based systems involves significantly changing formulation constituents. For example, if VOC's are reduced in the traditional anhydrous systems, they must be replaced with some suitable non-VOC ingredient. If that ingredient is water, the result is an aqueous based system and the traditional water insoluble resins must be replaced with water soluble resins. However, it has been found that hair sprays comprised of water soluble resins in an aqueous system are commercially unsatisfactory because these compositions cause hair to droop and become tacky under high humidity, and they prolong the drying time of the hair. In addition, the water beads which accumulate on hair are too large due to increased surface tension. These systems are also difficult to use with aerosol containers, often clogging the spray nozzle or causing system malfunction.

There is thus a need for hairsprays which contain less than 80% VOC's and yet provide an aesthetically pleasing commercial product.

SUMMARY OF THE INVENTION

The invention is directed to an aqueous aerosal hair spray comprising about 0.005-1.0% volatile silicone, 15-40% water/alcohol solution, 5-60% propellant, 1.0-10.0% water soluble resin, and 0.05-3.0% neutralizer/plasticizer.

The invention is directed to an anhydrous hairspray composition containing less than 80% VOC comprising 5-60% propellant, 1.0-10.0% resin, 0.05-3.0% neutralizer/plasticizer, and 50-98% alcohol.

The invention is also directed to a method for styling hair comprising spraying the hair with an effective amount of the compositions of the invention.

DETAILED DESCRIPTION

There are two preferred embodiments in the present invention. The first embodiment is directed to an aqueous hairspray composition containing less than 80% VOC's comprising about 0.005-1.0% volatile silicone, 15-40% water/alcohol solution, 5-60% propellant, 1.0-10.0% water soluble resin, and 0.05-3.0% neutralizer/plasticizer.

The volatile silicones suitable for use in the invention may be either cyclic or linear polydimethylsiloxanes. The term "volatile" means that the silicone has a measurable vapor pressure. The number of silicon atoms in the cyclic silicones is preferably from about 3 to about 7, more preferably 4 or 5. The general formula for such silicones is

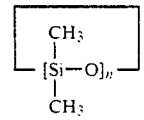

wherein n=3-7. The cyclic silicones generally have viscosities below 10 centistokes (cs) at 25° C.

The linear polydimethylsiloxanes have from about 3 to 9 silicone atoms and have the general formula $(CH_3)_3Si-O-Si(CH_3)_2-O-_n-Si(CH_3)_3$ where n=1-7. The linear volatile silicones generally have viscosities of less than about 5 centistokes at 25° C.

The cyclic silicones are preferred in the composition of the invention.

The term "neutralizer/plasticizer" means an ingredient which acts to make the resin less brittle. Plasticizers act to make the resins less brittle, and neutralizers act to make the resins more water soluble and by doing so make the resins less brittle, thereby exerting a plasticizing effect.

The term "propellant" in accordance with the invention means compositions used to effect propellant action in aerosol systems. Suitable propellants include n-butane, isobutane, dimethyl ether, difluoroethane, chlorodifluoroethane, chlorodifluoromethane, other chlorofluorocarbons, or mixtures thereof. Preferred propellants are dimethyl ether, 1,1-difluoroethane, n-butane, isobutane, or mixtures thereof. These propellants are manufactured by Dupont and are available under the trade names Dymel A, Dymel 152, Hydrocarbon A17, and Hydrocarbon A31. Similar propellants are also available commercially from a variety of other suppliers. The composition of the invention preferably contains a mixture of propellants, namely dimethyl ether, n-butane, and isobutane. Preferably the amount of propellant used in the composition ranges from 10-40%.

The water/alcohol solution generally comprises from about 4-6 parts water and about 6-4 parts alcohol, preferably so that the percentage of alcohol in the final composition is about 40-70% and the percentage of water in the final composition is is about 15-40%.

A variety of resins are suitable including vinyl acetate/crotonic acid/vinyl neodecanoate copolymer, octyl acrylamide/acrylates/butyl amino ethyl methacrylate copolymer, vinyl acetate/crotonic acid, polyvinylpyrollidone (PVP), polyvinyl pyrrolidone vinyl acetate copolymer, PVP Acrylates copolymer, etc Vinyl acetate/crotonic acid/vinyl neodecanoate copolymer is preferred.

It may be also desireable to incorporate other ingredients into the hair spray composition, such as moisturizers, fragrances, etc.

Preferably, a composition according to the invention contains all the constituents mentioned above and in addition, 0.001-1.0% surfactant. Surfactants reduce the surface tension between the aqueous and resin phase and allow for sprays containing a smaller droplet size or mist. Suitable surfactants include anionic, cationic, nonionic, or amphoteric surfactants having an HLB of 6-12, including PPG 28 Buteth 35, dimethicone copolyol, PEG 75 lanolin, perfluoropolymethyl isopropyl ether, polysiloxane polyether copolymers, octoxynol-9, PEG-25 hydrogenated castor oil, polyethylene terephthalate, polyethylene glycol 25 glyceryl trioleate, oleth-3 phosphate, PPG-5-ceteth-10 phosphate, PEG-20 methyl glucose ether, etc.

Suitable plasticizers or neutralizers include amino methyl propanol, polysorbate 80, acetylated lanolin alcohol, cetyl acetate, propylene glycol, lauramide DEA, dimethyl stearamine, laneth-10 acetate, laureth 10 acetate, PPG-20 methyl glucose ether.

If fragrance is incorporated into the composition, about 0.05-1% is suggested.

The composition may also contain 0.00001-3% moisturizers which are useful for providing a moisturizing effect to hair. Suitable moisturizers include hydrolyzed silk protein, panthenol, hydrolyzed wheat protein, etc.

The composition of the invention is capable of providing excellent holding power to hair without causing droop or tackiness under high humidity conditions. Furthermore, the composition works very well with standard aerosol containers and will not clog the nozzle or cause other undesireable effects.

The second preferred embodiment of the invention is an anhydrous hairspray composition containing less than 80% VOC's comprising 5-60% propellant, 1.0-10.0% resin, 0.05-3.0% neutralizer/plasticizer, and 50-98% alcohol.

Suitable alcohols are $C_{2-6}$ organic alcohols including ethanol, isopropanol, and the like.

The resins mentioned above are suitable and in addition other water insoluble resins such as the ethyl ester of Polyvinyl methacrylate/maleic anhydride (PVM/MA) copolymer, and the butyl ester of PVM/MA copolymer, and the like are suitable. Vinyl acetate/crotonic acid/vinyl neodecanoate copolymer, and amphomer resin or octylacrylamide/acrylates/butylaminoethyl methacrylate copolymer, PVP acrylates copolymer are preferred.

Suitable propellants include n-butane, isobutane, propane, dimethyl ether, difluoroethane, chlorodifluoroethane, chlorodifluoromethane, other chlorofluorocarbons, or mixtures thereof. N-butane, isobutane, and dimethyl ether are preferred.

These anhydrous compositions have very effective hair holding properties, yet contain less than 80% VOC.

The invention is also directed to a method for styling hair comprising spraying the hair with an effective amount of the hair spray composition of the invention.

The composition is applied in one or more short applications or sprays, and the hair dries almost instantly. The hair can be styled prior to spraying, and the applied spray will serve to set the hair.

The invention will be further described in connection with the following examples which are set forth for the purpose of illustration only.

EXAMPLE 1

An aqueous hair spray in accordance with the invention was made as follows:

|  | w/w % |
| --- | --- |
| Ethanol | 60.0 |
| Amino methyl propanol | 0.44 |
| Vinyl acetate/crotonic acid/ vinyl neodecanoate copolymer | 4.70 |
| Fragrance | 0.20 |
| Hydrolyzed silk protein | 0.0001 |
| Cyclomethicone | 0.100 |
| Water | 24.5599 |
| To 70% concentration | 100.00 |
| A31 | 10.00 |
| Dymel A | 20.00 |

A cold process was employed to make the hairspray. In a stainless steel vessel ethanol was charged and with propeller stirring the amino methyl propanol was added, followed by the vinyl acetate/crotonic acid polyer. The hydrolyze silk protein was slowly added while vortexing, and the fragrance, cyclomethicone, and water were added. Seventy percent or seventy parts of this solution was mixed with 10 parts of Hydrocarbon A31 and 20 parts Dymel A to make a 100 percent solution.

EXAMPLE 2

A anhydrous ultimate hold hairspray with less than 80% VOC was made as follows:

|  | w/w % | pref'd range |
| --- | --- | --- |
| SD-40B Alcohol | 92.8959 | 80-98 |
| Aminomethylpropanol | 0.634 | 0.1-1.0 |
| Vinyl acetate/crotonic acid/ vinyl neodecanoate copolymer | 5.0 | 2-10 |
| Polysorbate 80 | 0.20 | 0.1-1.0 |
| PPG 20 methyl glucose ether | 0.07 | .01-.10 |
| Fragrance | 0.20 | 0.1-0.5 |
| Hydrolyzed silk protein | 0.0001 | .00001-0.5 |
| Octylacrylamide/acrylates/butylaminoethyl Methacrylate copolymer | 1.000 | 0.25-2.0 |

Seventy parts of the above concentrate was mixed with 17% Dymel 152A and 13% A17 to yield a hairspray in compliance with 80% VOC limits.

EXAMPLE 3

An anhydrous extra hold hairspray was made as follows:

|  | w/w % | pref'd range |
| --- | --- | --- |
| SD 40B Alcohol | 94.7299 | 80-97 |
| Aminomethyl propanol | 0.40 | 0.1-1.0 |
| Vinyl acetate/crotonic acid/ vinyl neodecanoate copolymer | 4.25 | 2-10 |
| Polysorbate 80 | 0.20 | 0.1-1.0 |
| Laneth-10 acetate | 0.15 | 0.1-0.5 |
| PPG 20 Methyl glucose ether | 0.07 | .01-.10 |
| Fragrance | 0.20 | .1-0.5 |
| Hydrolyzed silk protein | 0.0001 | .00001-0.5 |

Seventy parts of the above solution was mixed with 17 parts Dymel 152A and 13 parts A17 to yield an extra hold hairspray within 80% VOC limits.

EXAMPLE 4

A water based extra hold hairspray was made as follows:

|  | w/w % | | | |
|---|---|---|---|---|
| Alcohol SD-40B | 60.00 | 60.00 | 60.00 | 60.00 |
| Amino methyl propanol | 0.44 | 0.44 | 0.44 | 0.44 |
| Vinyl acetate/crotonic acid/vinyl neodecanoate copolymer | 4.70 | 4.70 | 4.70 | 4.70 |
| Alcohol SD-40B | 10.00 | 10.00 | 10.00 | 10.00 |
| Dimethicone copolyol | 0.20 | 0.20 | 0.20 | — |
| Fragrance | — | — | — | 0.20 |
| Hydrolyzed silk protein | 0.0001 | 0.0001 | 0.0001 | 0.0001 |
| Water | 24.5599 | 24.5599 | 24.5599 | 24.5599 |
| Dimethicone | 0.10 | — | — | 0.10 |
| PPG 28 Buteth-35 | — | 0.10 | — | 0.10 |
| Cyclomethicone | — | — | 0.1 | — |

Seventy parts of the above solutions were mixed with 10 parts A31 and 20 parts Dymel A.

EXAMPLE 5

A water based ultimate hold hairspray was made as follows:

|  | w/w % | |
|---|---|---|
| Alcohol SD-40B | 60.00 | 60.00 |
| Aminomethyl propanol | 0.65 | 0.55 |
| Vinyl acetate/crotonic acid neodecanoate copolymer | 7.00 | 7.00 |
| Alcohol SD-40B | 7.0499 | 7.0499 |
| Fragrance | 0.20 | 0.20 |
| Hydrolyzed silk protein | 0.0001 | 0.0001 |
| Water | 25.00 | 25.00 |
| Cyclomethicone | 0.100 | 0.100 |

Seventy parts of the above solution was mixed with 10 parts of A31 and 20 parts of Dymel A to yield 100% composition.

While the invention has been described in connection with the preferred embodiment, it is not intended to limit the scope of the invention to the particular form set forth, but, on the contrary it is intended to cover such alternatives, modifications and equivalents as may be included within the spirit and scope of the invention as defined by the appended claims.

What is claimed is:

1. An aqueous aerosol hair spray composition consisting essentially of less than 80 percent volatile organic compounds, about 0.005-0.5% of a volatile silicone selected from the group consisting of cyclomethicone or dimethicone copolyol, 40-70% alcohol, 15-40% water, 5-60% of a propellant selected from the group consisting of a butane, isobutane, propane, dimethyl ether, difluoroethane, chlorodifluoroethane, chlorodifluoromethane, or mixtures thereof, 1.0-10.0% of a water soluble resin selected from the group consisting of vinyl acetate/crotonic acid/vinyl neodecanoate copolymer, octyl acrylamide/acrylates/butyl amino ethyl methacrylate copolymer, vinyl acetate/crotonic acid, polyvinylpyrollidone (PVP), PVP vinyl acetate copolymer, PVP acrylates copolymer, or mixtures thereof, 0.001-1.0% surfactants, and 0.05-3.0% neutralizer/plasticizer.

2. The composition of claim 1 wherein the water soluble resin is vinyl acetate/crotonic acid/vinyl neodecanoate copolymer.

3. The composition of claim 2 wherein the propellant is dimethyl ether, n-butane, isobutane, or mixtures thereof.

4. The composition of claim 3 wherein the surfactant is an anionic, cationic, nonionic, or amphoteric surfactant having an HLB of 6-12.

5. The composition of claim 4 wherein the plasticizer/neutralizer is amino methyl propanol, polysorbate 80, a mixture of polysorbate 80/acetylated lanolin alcohol, cetyl acetate, propylene glycol, laneth-10 acetate, lauramide DEA, dimethyl stearamine, laureth 10 acetate, PPG-20 methyl glucose ether, or mixtures thereof.

6. The composition of claim 5 additionally containing 0.05-5% fragrance.

7. A method for styling hair comprising spraying the hair with an effective amount of an aqueous aerosol hair spray consisting essentially of less than 80 percent volatile organic compounds, about 0.005-0.5% of a volatile silicone selected from the group consisting of cyclomethicone or dimethicone copolyol, 40-70% alcohol, 15-40% water, 5-60% of a propellant selected from the group consisting of n-butane, isobutane, propane, dimethyl ether, difluoroethane, chlorodifluoroethane, chlorodifluoromethane, r mixtures hereof, 1.0-10.0% of a water soluble resin selected from the group consisting of vinyl acetate/crotonic acid/vinyl neodecanoate copolymer, octyl acrylamide/acrylates/butyl amino ethyl methacrylate copolymer, vinyl acetate/crotonic acid, polyvinylpyrollidone (PVP), PVP vinyl acetate copolymer, PVP acrylates copolymer, or mixtures thereof, 0.001-1.0% surfactant, and 0.05-3.0% neutralizer/plasticizer.

8. The method of claim 7 wherein the composition is applied after styling the hair.

9. An anhydrous hairspray composition consisting essentially of less than 80% VOC, 5-60% of a propellant selected from the group consisting of n-butane, isobutane, propane, dimethyl ether, difluoroethane, chlorodifluoroethane, chlorodifluoromethane, or mixtures thereof, 1.0-10.0% of a resin selected from the group consisting of the ethyl ester of polyvinyl methacrylate/maleic anhydride (PVM/MA) copolymer, butyl ester of PVM/MA copolymer, vinyl acetate/crotonic acid/vinyl neodecanoate copolymer, the amphomer resin of octylacrylamide/acrylates/butyl aminoethyl methacrylate copolymer, PVP acrylates copolymer, or mixtures thereof, 0.05-3.0% neutralizer/plasticizer, and 80-98% alcohol.

10. The composition of claim 9 wherein the alcohol is ethanol.

11. The composition of claim 10 wherein the propellant is selected from the group consisting of dimethyl ether, n-butane, isobutane, or mixtures thereof.

12. A method for styling hair comprising applying to the hair an effective amount of an anhydrous hairspray composition consisting essentially of less than 80 percent VOC, 5-60% of a propellant selected from the group consisting of n-butane, isobutane, propane, dimethyl ether, difluoroethane, chlorodifluoroethane, chlorodifluoromethane, or mixtures thereof, 1.0-10.0% of a resin selected from the group consisting of the ethyl ester of polyvinyl methacrylate/maleic anhydride (PVM/MA) copolymer, butyl ester of PVM/MA copolymer, vinyl acetate/crotonic acid/vinyl neodecanoate copolymer, the amphomer resin of octylacrylamide/acrylates/butyl aminoethyl methacrylate copolymer, PVP acrylates copolymer, or mixtures thereof, 0.05-3.0% neutralizer/plasticizer, and 80-98% alcohol.

13. An anhydrous hairspray composition containing less than 80% VOC, which contains about 70 parts of a Composition A comprising:
   a) 80-98% SD-40B alcohol,
   b) 0.1-1.0% amino methyl propanol,
   c) 2-10% vinyl acetate/crotonic acid/vinyl neodecanoate copolymer,
   d) 0.1-1.0% Polysorbate 80,
   e) 0.01-0.10% PPG-20 methyl glucose ether,
   f) 0.1-0.5% fragrance,
   g) 0.00001-0.5% hydrolyzed silk protein,
   and about 30 parts of a propellant selected from the group consisting of dimethyl ether, 1-1, difluoroethane, n-butane, isobutane, or mixtures thereof.

14. The composition of claim 13 where Composition A additionally comprises 0.25-2.0% octylacrylamide/acrylates butyl aminoethyl methacrylate copolymer.

15. An aqueous aerosol hair spray composition consisting essentially of less than 80 percent volatile organic compounds, about 0.005-0.5% of a volatile silicone selected from the group consisting of cyclomethicone or dimethicone copolyol, 40-70% alcohol, 15-40% water, 5-60% propellant selected from the group consisting of n-butane, isobutane, propane, dimethyl ether, difluoroethane, chlorodifluoroethane, chlorodifluoromethane, or mixtures thereof, 1.0-10.0% of a water soluble resin selected from the group consisting of vinyl acetate/crotonic acid/vinyl neodecanoate copolymer, octyl acrylamide/acrylates/butyl amino ethyl methacrylate copolymer, vinyl acetate/crotonic acid, polyvinylpyrollidone (PVP), PVP vinyl acetate copolymer, PVP acrylates copolymer, or mixtures thereof, 0.001-1.0% surfactant, 0.00001-3% moisturizers, and 0.05-3.0% neutralizer/plasticizer.

16. The composition of claim 15 wherein the moisturizer is hydrolyzed silk protein.

* * * * *